US00PP20045P2

(12) United States Plant Patent
Wood

(10) Patent No.: US PP20,045 P2
(45) Date of Patent: Jun. 2, 2009

(54) ***HYPERICUM* PLANT NAMED 'DEPPE'**

(50) Latin Name: *Hypericum kalmianum*
Varietal Denomination: Deppe

(75) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 12/075,450

(22) Filed: Mar. 11, 2008

(51) Int. Cl.
*A01H 5/00* (2006.01)

(52) U.S. Cl. ..... Plt./442
(58) Field of Classification Search ..... Plt./442
See application file for complete search history.

*Primary Examiner*—S. B McCormick Ewoldt
(74) *Attorney, Agent, or Firm*—C. A. Whealy

(57) ABSTRACT

A new and distinct cultivar of *Hypericum* plant named 'Deppe', characterized by its compact and uniformly mounding plant habit; dark green-colored leaves; freely flowering habit; large bright yellow-colored flowers; and good garden performance.

1 Drawing Sheet

Figure 1:
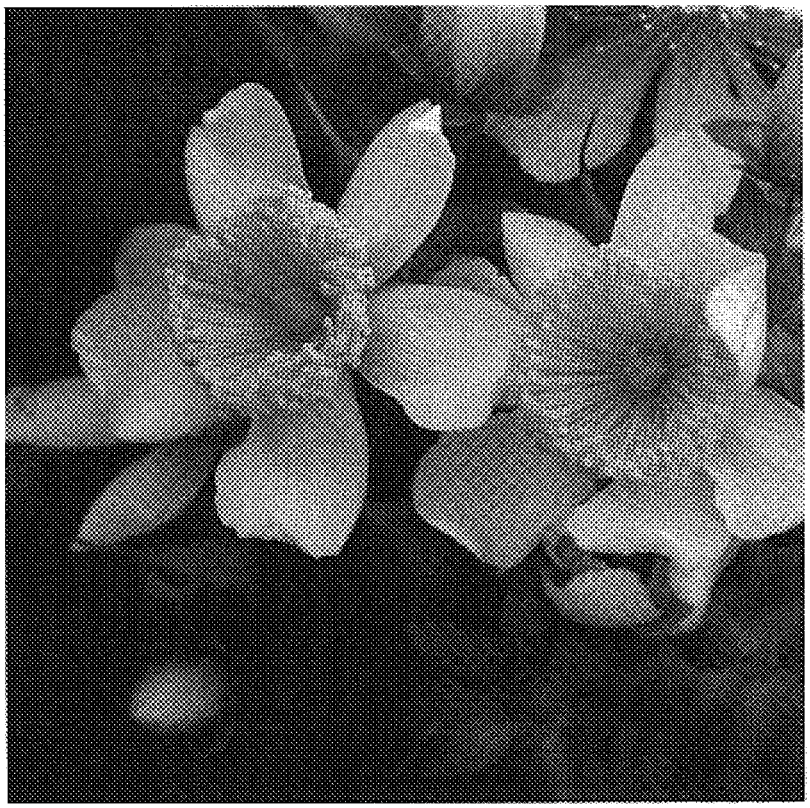
Figure 2:
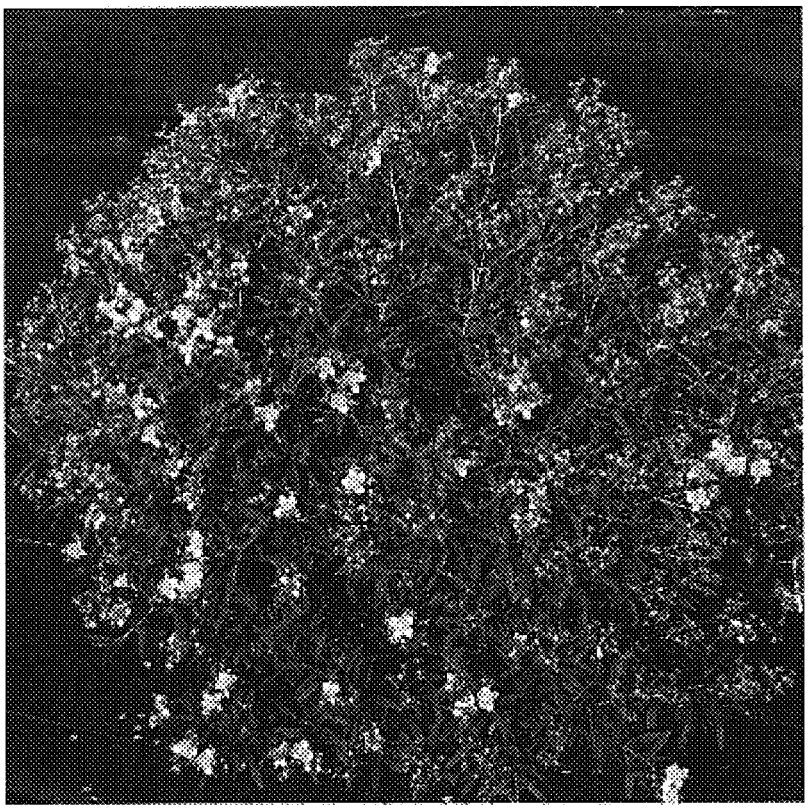

Botanical designation: *Hypericum kalmianum.*
Cultivar denomination: 'DEPPE'.

BACKGROUND OF THE INVENTION

The present invention relates to a new and distinct cultivar of *Hypericum,* botanically known as *Hypericum kalmianum* and hereinafter referred to by the name 'Deppe'.

The new *Hypericum* is a product of a planned breeding program conducted by the Inventor in Grand Haven, Mich. The objective of the breeding program is to create new *Hypericum* cultivars with uniform plant habit and numerous attractive flowers.

The new *Hypericum* originated from an open-pollination during the summer of 2002 in Grand Haven, Mich. of the *Hypericum kalmianum* cultivar Gemo, not patented, as the female, or seed parent with an unknown selection of *Hypericum kalmianum,* as the male, or pollen, parent. The new *Hypericum* was discovered and selected by the Inventor as a single flowering plant within the progeny of the stated open-pollination in a controlled environment in Grand Haven, Mich. during the summer of 2004.

Asexual reproduction of the new cultivar by softwood cuttings in Grand Haven. Mich., since the summer of 2004, has shown that the unique features of this new *Hypericum* are stable and reproduced true to type in successive generations.

SUMMARY OF THE INVENTION

Plants of the cultivar Deppe have not been observed under all possible environmental conditions. The phenotype may vary somewhat with variations in environment such as temperature and light intensity without, however, any variance in genotype.

The following traits have been repeatedly observed and are determined to be the unique characteristics of 'Deppe'. These characteristics in combination distinguish 'Deppe' as a new and distinct cultivar of *Hypericum:*

1. Compact and uniformly mounding plant habit.
2. Dark green-colored leaves.
3. Freely flowering habit.

4. Large bright yellow-colored flowers.
5. Good garden performance.

Plants of the new *Hypericum* differ from plants of the female parent, the cultivar Gemo, in the following characteristics:

1. Plants of the new *Hypericum* are more compact than and not as open as plants of the cultivar Gemo.
2. Plants of the new *Hypericum* have darker green-colored leaves than plants of the cultivar Gemo.
3. Plants of the new *Hypericum* are more freely flowering than plants of the cultivar Gemo.

Plants of the new *Hypericum* can be compared to plants of the cultivar Ames, not patented. In side-by-side comparisons conducted by the Inventor in Grand Haven, Mich., plants of the new *Hypericum* differed from plants of the cultivar Ames in the following characteristics:

1. Plants of the new *Hypericum* were more compact than and not as open as plants of the cultivar Ames.
2. Plants of the new *Hypericum* had darker green-colored leaves than plants of the cultivar Ames.
3. Plants of the new *Hypericum* were more freely flowering than plants of the cultivar Ames.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Hypericum.*

The photograph at the bottom of the sheet comprises a side perspective view of a typical flowering plant of 'Deppe' grown in a container.

The photograph at the top of the sheet is a close-up view of typical flowers of 'Deppe'.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photographs and following description were grown under conditions which closely approximate commercial production conditions during the spring and summer in an outdoor nursery in Grand Haven, Mich. Plants used for the photographs and description were about three years old.

Botanical classification: *Hypericum kalmianum* cultivar Deppe.

Parentage:

*Female, or seed, parent.*—*Hypericum kalmianum* cultivar Gemo, not patented.

*Male, or pollen, parent.*—Unknown selection of *Hypericum kalmianum,* not patented.

Propagation:

*Type cutting.*—Softwood cuttings.

*Time to initiate roots.*—About 20 days at 22° C.

*Time to produce a rooted young plant.*—About two months at 22° C.

*Root description.*—Fine, fibrous.

*Rooting habit.*—Freely branching; dense.

Plant description:

*Form.*—Compact and uniformly mounding plant form; roughly spherical in shape. Freely branching with about 87 lateral stems developing per plant; dense and bushy plant form; vigorous growth habit.

*Plant height.*—About 30 cm.

*Plant width* (*spread*).—About 35 cm.

*Lateral branch description.*—Length: About 24 cm. Diameter: About 3 mm. Internode length: About 1.5 cm. Strength: Strong. Texture: Smooth, glabrous. Color: Close to 144A.

Foliage description:

*Arrangement.*—Opposite, simple.

*Length.*—About 6 cm.

*Width.*—About 1.2 cm.

*Shape.*—Lanceolate.

*Apex.*—Obtuse.

*Base.*—Cuneate.

*Margin.*—Entire.

*Texture, upper and lower surfaces.*—Smooth, glabrous.

*Venation pattern.*—Pinnate.

*Color.*—Developing foliage, upper and lower surfaces: 136A. Fully expanded foliage, upper surface: 147A; venation, close to 138B. Fully expanded foliage, lower surface: 147B; venation, 138B.

*Petioles.*—Length: About 5 mm. Width: About 2 mm. Texture, upper and lower surfaces: Smooth, glabrous. Color, upper and lower surfaces: 138B.

Flower description:

*Flower arrangement and shape.*—Bright yellow-colored single flowers arranged in terminal cymes; freely flowering habit with about 41 flowers per cyme. Flowers not persistent. Flowers face mostly upright to outwardly.

*Fragrance.*—None detected.

*Natural flowering season.*—Typically July in Grand Haven, Mich.; flowers last about three to five days on the plant.

*Flower buds.*—Length: About 8 mm. Diameter: About 5 mm. Shape: Ovate. Color: 151B.

*Inflorescence size.*—Height: About 9 cm. Diameter: About 10 cm.

*Flowers.*—Diameter: About 2.5 cm. Depth (height): About 7 cm.

*Petals.*—Quantity/arrangement: Five in a single whorl. Length: About 1.5 cm. Width: About 7 mm. Shape: Elliptic to ovate. Apex: Obtuse. Base: Attenuate. Margin: Entire. Texture, upper and lower surfaces: Smooth, glabrous. Color: When opening and fully opened, upper surface: 5A. When opening and fully opened, lower surface: 5A.

*Sepals.*—Quantity/arrangement: Five or occasionally six in a single whorl. Length: About 9 mm. Width: About 3 mm. Shape: Narrowly elliptic to lanceolate. Apex: Acute. Base: Cuneate. Margin: Entire. Texture, upper and lower surfaces: Smooth, glabrous. Color: When opening, upper and lower surfaces: 147B. Fully opened, upper and lower surfaces: 147B.

*Peduncles.*—Strength: Strong. Length: About 1 cm to 2.2 cm. Diameter: About 2.2 mm. Aspect: Erect to about 45° from vertical. Texture: Smooth, glabrous. Color: 144B.

*Pedicels.*—Strength: Strong. Length: About 1 cm. Diameter: About 1.5 mm. Aspect: Erect to about 45° from the stem axis. Texture: Smooth, glabrous. Color: 144B.

*Reproductive organs.*—Stamens: Quantity per flower: About 200. Anther shape: Rounded. Anther length: Less than 0.5 mm. Anther color: 5A. Pollen amount: Abundant. Pollen color: 5A. Pistils: Quantity per flower: One. Pistil length: About 8 mm. Stigma shape: Rounded. Stigma color: 151B. Style length: About 4 mm. Style color: 151B. Ovary color: 151B.

*Seeds.*—Length: Less than 0.5 mm. Diameter: Less than 0.5 mm. Color: Close to 200A.

Disease/pest resistance: Plants of the new *Hypericum* have not been noted to be resistant to pathogens and pests common to *Hypericum.*

Garden performance: Plants of the new *Hypericum* have exhibited good garden performance tolerating rain, wind and temperatures ranging from about −27° C. to about 37° C.

It is claimed:

1. A new and distinct *Hypericum* plant named 'Deppe' as illustrated and described.

* * * * *